United States Patent
Schietinger et al.

(10) Patent No.: US 6,799,137 B2
(45) Date of Patent: Sep. 28, 2004

(54) WAFER TEMPERATURE MEASUREMENT METHOD FOR PLASMA ENVIRONMENTS

(75) Inventors: Charles W. Schietinger, Milwaukie, OR (US); Ronald A. Palfenier, Oregon City, OR (US)

(73) Assignees: Engelhard Corporation, Iselin, NJ (US); Exactus, Inc., Boca Raton, FL (US)

( * ) Notice: Subject to any disclaimer, the term of this patent is extended or adjusted under 35 U.S.C. 154(b) by 65 days.

(21) Appl. No.: 10/197,230

(22) Filed: Jul. 16, 2002

(65) Prior Publication Data

US 2003/0033110 A1 Feb. 13, 2003

Related U.S. Application Data

(63) Continuation-in-part of application No. 09/872,752, filed on Jun. 1, 2001, now Pat. No. 6,647,350.
(60) Provisional application No. 60/307,422, filed on Jul. 23, 2001, provisional application No. 60/209,168, filed on Jun. 2, 2000, provisional application No. 60/209,074, filed on Jun. 2, 2000, provisional application No. 60/209,076, filed on Jun. 2, 2000, and provisional application No. 60/217,012, filed on Jul. 10, 2000.

(51) Int. Cl.[7] .......................... G01K 11/30; G06F 15/00
(52) U.S. Cl. ...................................................... 702/134
(58) Field of Search ................................. 702/134, 136, 702/99; 374/120, 121, 123; 250/370.15; 118/715

(56) References Cited

U.S. PATENT DOCUMENTS

| | | |
|---|---|---|
| 1,475,365 A | 11/1923 | Schueler et al. |
| 1,639,534 A | 8/1927 | Ruben |
| 2,709,367 A | 5/1955 | Bohnet |
| 3,262,758 A | 7/1966 | Stewart et al. |
| 4,075,493 A | 2/1978 | Wickersheim |
| 4,348,110 A | 9/1982 | Ito |
| 4,574,486 A | 3/1986 | Drechsler |
| 4,750,139 A | 6/1988 | Dils |
| 4,845,647 A | 7/1989 | Dils et al. |
| 4,956,538 A | 9/1990 | Moslehi |
| 5,154,512 A | 10/1992 | Schietinger et al. |
| 5,231,595 A * | 7/1993 | Makino et al. ............. 702/134 |
| 5,305,416 A * | 4/1994 | Fiory .......................... 392/416 |
| 5,624,590 A * | 4/1997 | Fiory .......................... 219/390 |

(List continued on next page.)

OTHER PUBLICATIONS

"Optical Pyrometry Begins to Fulfill its Promise," Alexander Braun, Semiconductor International, Mar. 1998, pp. 1 and 2.

(List continued on next page.)

Primary Examiner—John Barlow
Assistant Examiner—Demetrius R. Pretlow
(74) Attorney, Agent, or Firm—Stoel Rives LLP

(57) ABSTRACT

The temperature of a semiconductor wafer (160) is measured while undergoing processing in a plasma (168) environment. At least two pyrometers (162, 164) receive radiation from, respectively, the semiconductor wafer and the plasma in a plasma process chamber. The first pyrometer receives radiation from either the front or rear surface of the wafer, and the second pyrometer receives radiation from the plasma. Both pyrometers may be sensitive to the same radiation wavelength. A controller (170) receives signals from the first and second pyrometers and calculates a corrected wafer emission, which is employed in the Planck Equation to calculate the wafer temperature. Alternatively, both pyrometers are positioned beneath the wafer with the first pyrometer sensitive to a first wavelength where the wafer is substantially opaque to plasma radiation, and the second pyrometer is sensitive to a wavelength where the wafer is substantially transparent to plasma radiation.

24 Claims, 12 Drawing Sheets

U.S. PATENT DOCUMENTS

| | | | | |
|---|---|---|---|---|
| 5,696,863 A | * | 12/1997 | Kleinerman | 385/123 |
| 5,717,608 A | | 2/1998 | Jensen | |
| 5,769,540 A | * | 6/1998 | Schietinger et al. | 374/127 |
| 5,815,410 A | | 9/1998 | Heinke et al. | |
| 5,897,610 A | | 4/1999 | Jensen | |
| 5,930,456 A | * | 7/1999 | Vosen | 392/416 |
| 5,997,175 A | * | 12/1999 | Champetier et al. | 374/126 |
| 6,007,241 A | | 12/1999 | Yam et al. | |
| 6,160,242 A | * | 12/2000 | Guardado | 219/390 |
| 6,191,392 B1 | * | 2/2001 | Hauf et al. | 219/411 |
| 6,299,346 B1 | * | 10/2001 | Ish-Shalom et al. | 374/126 |
| 6,325,536 B1 | * | 12/2001 | Renken et al. | 374/161 |

OTHER PUBLICATIONS

"A New Detector for IRLED Light," Russ Dahl and Michael Allen, reprinted from SENSORS Magazine, Dec. 1996, 4 pp.

RTA T/C and RT Measurements, B.E. Adams, Workshop on Temp. Meas. of Semi. Wafers Using Thermocouples, RTP'2000 confernece, Gaithersburg, Maryland, Sep. 19, 2000.

A Review of Wafer Temperature Measurement Using Optical Fibers and Ripple Pyrometry, C. Schietinger, 5th International Rapid Thermal Processing Conference RTP' 97, New Orleans, LA, Sep. 3–5, 1997.

Advances in Rapid Thermal and Integrated Processing, Chapter 3 and 4, Editor F. Roozeboom, Kluwer Academic Publishers, The Netherlands, 1996.

Wafer Temperature Measurement: Status Utilizing Optical Fibers, C. Schietinger, Proc. Symp. Mat. Res. Soc., San Francisco, Apr. 8–12, 1996.

"MAXLINE BCS Background Compensation System", Ircon, Inc., Niles, Illinois, Feb., 1998, pp. 1–8.

* cited by examiner

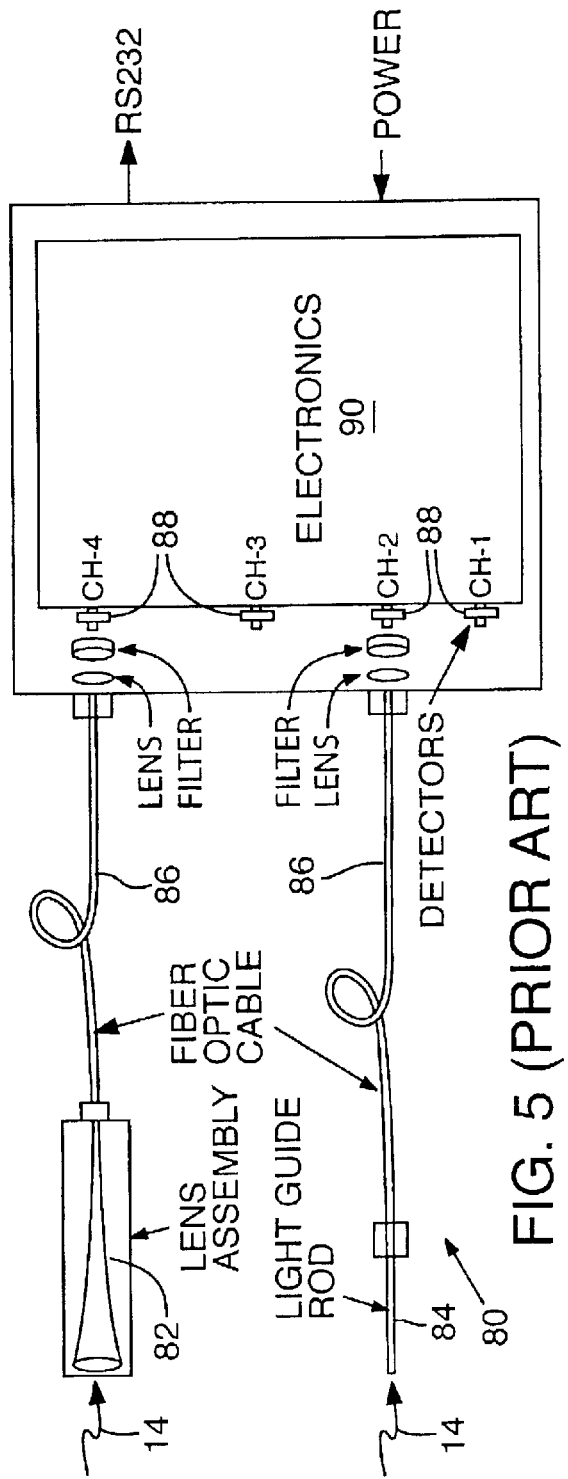
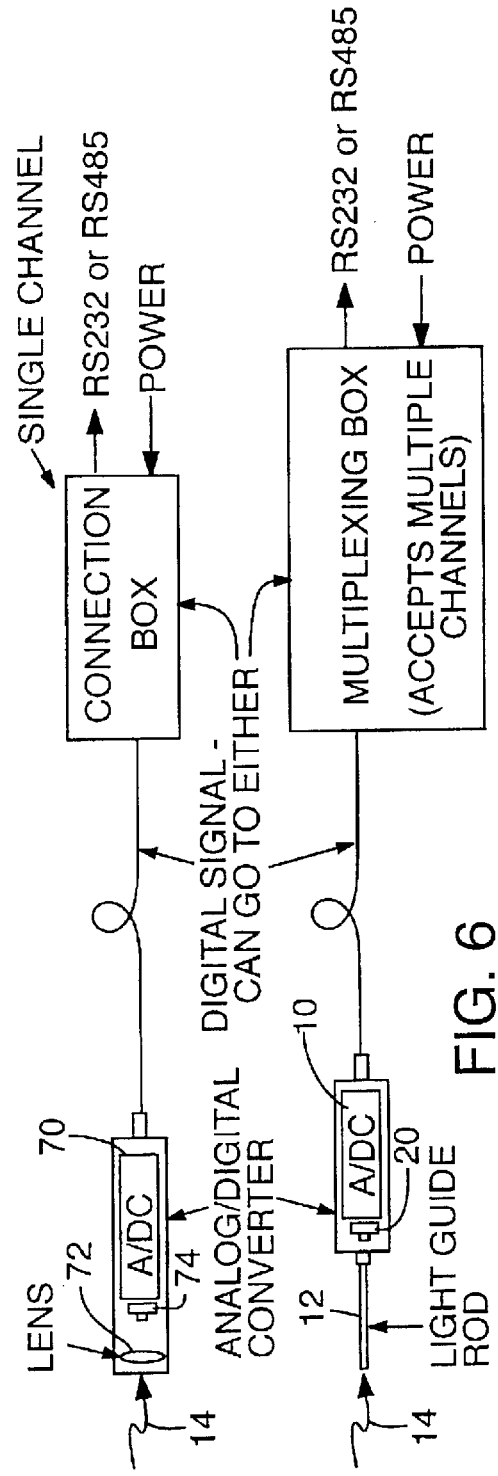
FIG. 5 (PRIOR ART)
FIG. 6

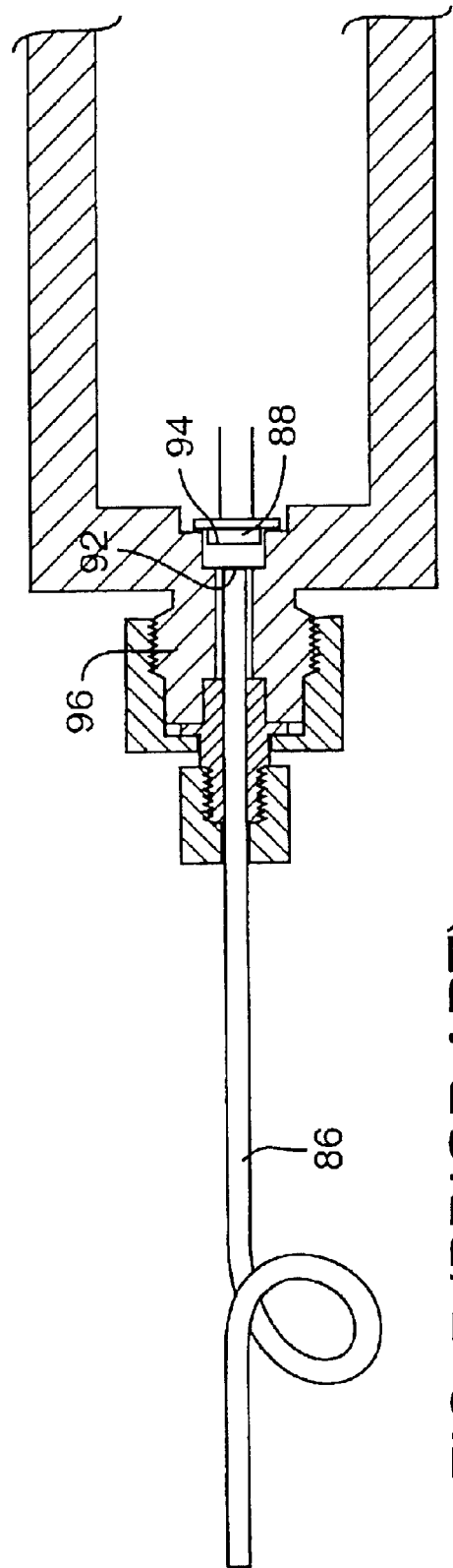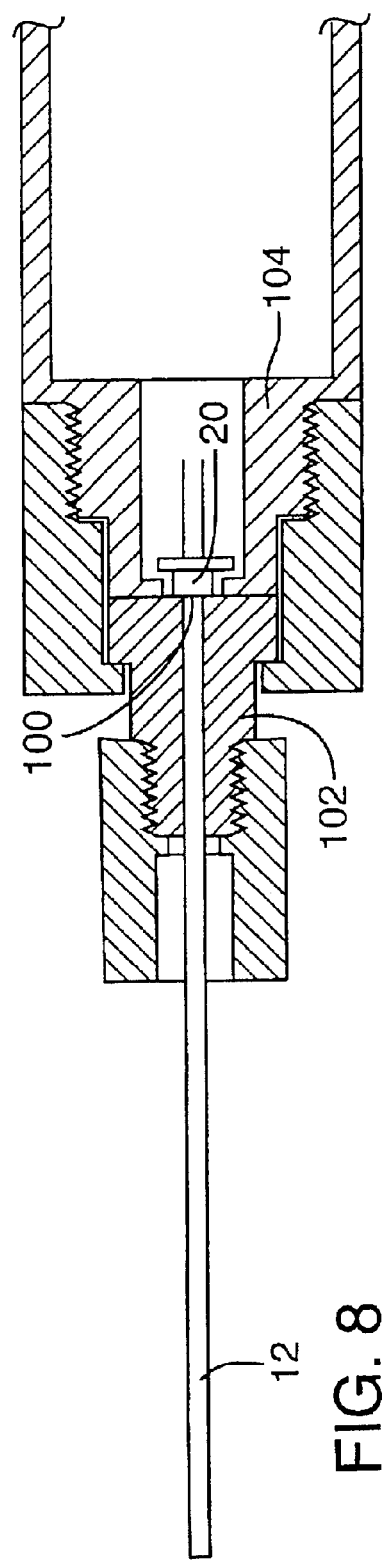
FIG. 7 (PRIOR ART)
FIG. 8

WAFER TEMPERATURE MEASUREMENT METHOD FOR PLASMA ENVIRONMENTS

RELATED APPLICATIONS

This application claims priority from U.S. Provisional application No. 60/307,422, filed Jul. 23, 2001, and is a continuation-in-part of U.S. patent application Ser. No. 09/872,752, filed Jun. 1, 2001, now U.S. Pat. No. 6,647,350 which claims priority from U.S. Provisional Application Nos. 60/209,168; 60/209,074; and 60/209,076; all filed Jun. 2, 2000, and Ser. No. 60/217,012, filed Jul. 10, 2000.

FEDERALLY SPONSORED RESEARCH OR DEVELOPMENT

Not applicable

TECHNICAL FIELD

This invention relates to radiometric temperature measurement systems (also known as "pyrometers") and more particularly to a measurement method employing a pyrometer system having improved low temperature measurement sensitivity for determining a surface temperature of a semiconductor wafer or an object without contacting its surface.

BACKGROUND OF THE INVENTION

Pyrometer-based temperature measurement systems have a long development history. For example, even before 1930, U.S. Pat. Nos. 1,318,516; 1,475,365; and 1,639,534 all described early pyrometers. In 1933, U.S. Pat. No. 1,894,109 to Marcellus described a pyrometer employing an optical "lightpipe." In 1955, U.S. Pat. No. 2,709,367 to Bohnet described a pyrometer in which sapphire and curved sapphire lightpipes are used in collection optics. In 1971, U.S. Pat. No. 3,626,758 to Stewart described using quartz and sapphire lightpipes with a blackbody sensor tip. Then in 1978, U.S. Pat. No. 4,075,493 to Wickersheim described a modern flexible fiber optic thermometer.

In the 1980s, U.S. Pat. No. 4,348,110 to Ito described electronic improvements to pyrometers, such as an integrating photo-detector output circuit. Then U.S. Pat. Nos. 4,576,486, 4,750,139, and 4,845,647, all to Dils, described further improvements to electronics, fiber-optics, sapphire rods, and blackbody emission temperature measurements.

In the 1990s, many patents issued that describe the use of pyrometers in semiconductor processing. For example, in 1990, U.S. Pat. No. 4,956,538 to Moslehi described using fiber optic lightpipes for wafer temperature measurements in rapid thermal processing ("RTP") applications. In 1992, U.S. Pat. No. 5,154,512 to Schietinger described using a fiber optic thermometer with wavelength selective mirrors and modulated light to measure semiconductor wafer temperatures. In 1998, U.S. Pat. No. 5,717,608 to Jenson described using an integrating amplifier chip and fiber-optics to measure semiconductor wafer temperatures, and U.S. Pat. No. 5,815,410 to Heinke described an infrared ("IR") sensing thermometer using an integrating amplifier. Then in 1999, U.S. Pat. No. 5,897,610 to Jensen described the benefits of cooling pyrometers, and U.S. Pat. No. 6,007,241 to Yam described yet another fiber optic pyrometer for measuring semiconductor wafer temperatures.

As one can see from these prior patents, pyrometer systems are commonly used for measuring the temperature of semiconductor silicon wafers housed within a process chamber while forming integrated circuits ("ICs") on the wafer. Virtually every process step in silicon wafer fabrication depends on the measurement and control of wafer temperature. As wafer sizes increase and the critical dimension of very large scale ICs scales deeper into the submicron range, the requirements for wafer-to-wafer temperature repeatability during processing become ever more demanding.

Processes such as physical vapor deposition ("PVD"), high-density plasma chemical vapor deposition ("HDP-CVD"), epitaxy, and RTP can be improved if the wafer temperature is accurately measured and controlled during processing. In RTP there is a special importance to temperature monitoring because of the high temperatures and the importance of tightly controlling the thermal budget, as is also the case for Chemical Mechanical Polishing ("CMP") and Etch processes.

As wafer sizes increase, the cost of each wafer increases geometrically, and the importance of high quality in-process temperature monitoring increases accordingly. Inadequate wafer temperature control during processing reduces fabrication yields and directly translates to lost revenues.

In addition to conventional pyrometry, the most common in-situ temperature sensing techniques employed by semiconductor processing wafer fabs and foundries also includes thermocouples and advanced pyrometry.

Thermocouples are easy to use, but their reliability and accuracy are highly questionable. Thermocouples are only accurate when the wafer is in thermal equilibrium with its surroundings and the thermocouple is contacting or embedded in that environment. Otherwise, the thermocouple reading might be far from the correct wafer temperature. For example, in PVD applications, while the thermocouple embedded in the heated chuck provides a temperature measurement that resembles that of the wafer, there are large offsets between the wafer and the thermocouple. These offsets are a function of gas pressure and heat transfer.

In conventional optical pyrometry, a pyrometer deduces the wafer temperature from the intensity of radiation emitted by the wafer. The pyrometer typically collects the radiation from the wafer through an interface employing a lens or a quartz or sapphire rod. Such interfaces have been used with PVD, HDP-CVD, RTP, Etch, and rapid thermal chemical vapor deposition ("RTCVD"). While conventional optical pyrometers are often superior to the use of thermocouples, there are measurement inaccuracy problems caused by the processing environment, such as background light, wafer transmission, emissivity, and signal-to-noise ratio problems that cannot be ignored.

Advanced pyrometry offers some satisfactory temperature monitoring solutions for semiconductor wafer production applications. "Optical Pyrometry Begins to Fulfill its Promise," by Braun, Semiconductor International, March 1998, describes advanced pyrometry methods that overcome some limitations of conventional pyrometry. As such, optical pyrometers and fiber optic thermometers employing the Planck Equation are now commonly used for in-situ semiconductor wafer measurement. However, numerous problems and limitations are still encountered when measuring wafer temperature using "Planck" radiation (light) emitted by the wafer. There are numerous problems when measuring wafers at temperatures below about 400° C.: 1) minimal signal levels generated by the photo detector (as small as 1E–16 amps) because the very small amount of radiation emitted by the wafer; 2) the wafer is semi-transparent at low temperatures and long wavelengths (greater than 900 nm); and 3) the background light is often larger than the emitted wafer signal and causes large errors when it enters the collection optics. Moreover, electromagnetic radiation transmission losses and the emissivity of the object being measured is often unknown and changing, which increases the difficulty of achieving accurate temperature measurements.

What is still needed, therefore, is an advanced pyrometer system and measurement method that provides accurate and repeatable temperature measurements of an object, such as a semiconductor wafer, down to about room temperature without contacting the object being measured.

SUMMARY OF THE INVENTION

An object of this invention is, therefore, to provide an apparatus and a method for performing non-contacting temperature measurements of target media.

Another object of this invention is to provide an advanced pyrometer system capable of measuring semiconductor wafer temperatures down to or below about room temperature.

A further object of this invention is to provide an advanced pyrometer system and method for making high accuracy semiconductor wafer temperature measurements in a plasma processing environment.

An advanced pyrometer system of this invention has reduced optical losses, better background radiation blocking, improved signal-to-noise ratio, and improved signal processing to achieve improved accuracy and temperature measurement capabilities ranging from about 10° C. to about 4,000° C.

The system includes collection optics that acquire emitted radiation from a hot specimen and directly couples it to an optional filter and a photo detector. The collection optics may include lens systems, optic lightpipes, and flexible fiber optics. The preferred collection optic is a yttrium-aluminum-garnet ("YAG") light guide rod. The filter or filters employed are wavelength-selective to determine which radiation wavelengths are measured, and optionally includes a hot/cold mirror surface for reflecting undesired radiation wavelengths back to the specimen. The photo detectors are formed from silicon, InGaAs or, preferably, doped AlGaAs having narrow bandpass detection characteristics centered near 900 nm. The doped AlGaAs detector allows eliminating the optical filter, in some applications, if additional detection sensitivity is required. Also, light at wide angles has less effect on the wavelength sensitivity of the AlGaAs detector.

The system further includes an amplifier that acquires and conditions signals as small as 10–16 amps for detection and measurement. A signal processor converts the amplified signal into a temperature reading. This processing is a combination of electrical signal conditioning, analog-to-digital conversion, correction factors, and software algorithms, including the Planck equation.

In a preferred embodiment, the temperature of a semiconductor wafer is measured while undergoing processing in a plasma environment. At least two pyrometers receive radiation from, respectively, the semiconductor wafer and background light from a plasma in a plasma etch, strip, or deposition process chamber. The first pyrometer receives radiation from either the front or rear surface of the wafer, and the second pyrometer receives radiation from the plasma. In this embodiment, both pyrometers may be sensitive to the same radiation wavelength.

A central processor unit or controller receives signals from the first and second pyrometers and calculates a corrected wafer emission, which is employed in the Planck Equation to calculate the wafer temperature.

In an alternate embodiment of this invention, both pyrometers are positioned beneath the wafer. The first pyrometer is sensitive at a first wavelength where the wafer is substantially opaque to plasma radiation, and the second pyrometer is sensitive at a wavelength where the wafer is substantially transparent to plasma radiation.

Additional objects and advantages of this invention will be apparent from the following detailed description of preferred embodiments thereof that proceed with reference to the accompanying drawings.

BRIEF DESCRIPTION OF THE DRAWINGS

FIG. 5 is a simplified pictorial view of a prior art pyrometer system employing optical fiber cables to couple emitted radiation to detectors.

FIG. 6 is a simplified pictorial view of a pyrometer system of this invention employing direct coupling of emitted radiation to detectors.

FIG. 7 is a sectional side view of a prior art light guide rod and detector mounting system in which the optical faces of the light guide rod and detector are recessed within threaded housings making cleaning difficult.

FIG. 8 is a sectional side view of a light guide rod and detector mounting system of this invention in which the optical faces of the light guide rod and detector are flush to the edges of their respective housings and, therefore, easy to clean.

DETAILED DESCRIPTION OF PREFERRED EMBODIMENTS

This application is based on inventions described in Provisional application No. 60/307,422, filed Jul. 23, 2001, and application Ser. No. 09/872,752, filed Jun. 1, 2001, both of which are assigned to the assignee of this application and are incorporated herein by reference.

Figure 1:
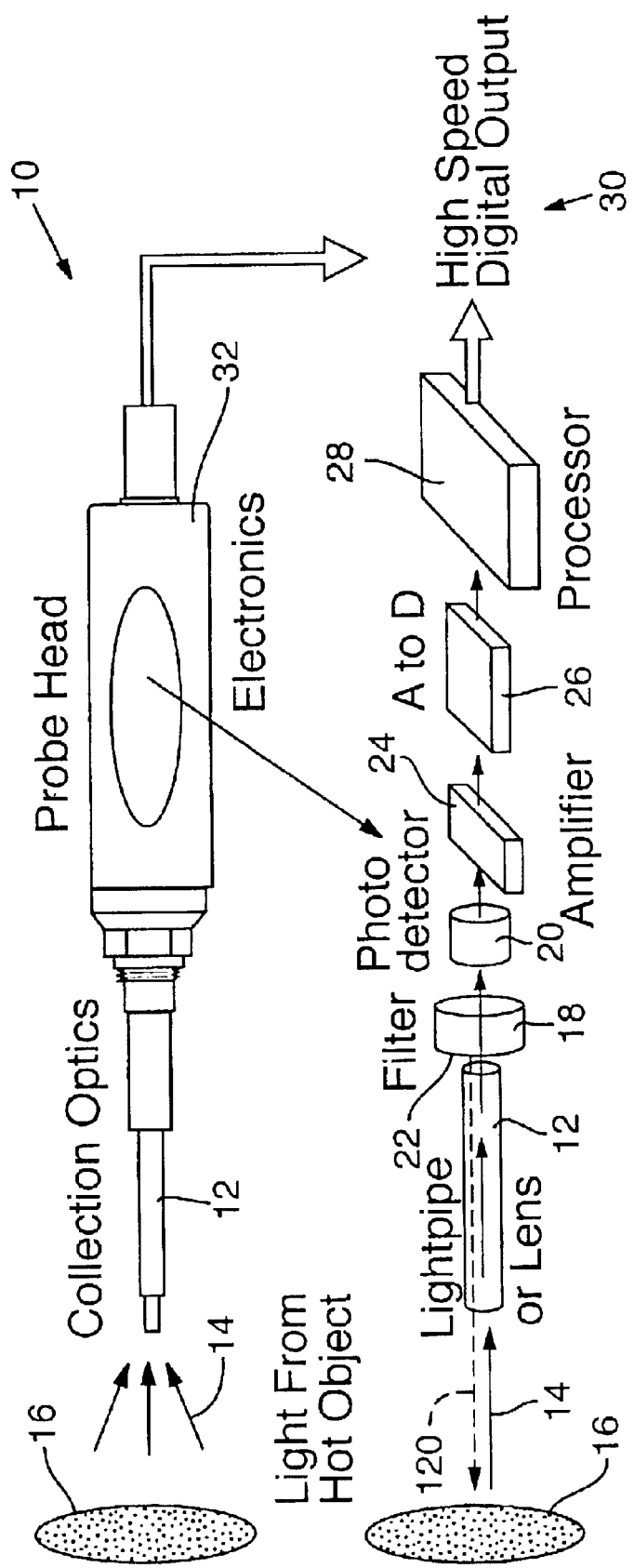
FIG. 1 is a combined pictorial and corresponding schematic block diagram of an pyrometer system of this invention.

FIG. 1 shows a radiometric system 10 of this invention, which includes collection optics 12 for acquiring emitted radiation 14 from a target medium, such as an object 16. Collection optics 12 direct radiation 14 to a wavelength selective filter 18 and a photo detector 20. Collection optics 12 may alternatively include rigid or flexible fiber optic light pipes and/or a lens system for measuring the temperature of predetermined areas on object 16. The target medium may include gases, plasmas, heat sources, and other non-solid target media.

Wavelength selective filter 18 selects which wavelengths of radiation 14 are measured. A preferred embodiment of filter 18 includes a hot/cold mirror surface 22 for reflecting unneeded wavelengths of radiation 14 back toward object 16. Skilled workers will recognize that filter 18 and hot/cold mirror surface 22 should be housed to maintain them in a clean and dry condition.

Photo detector 20 converts radiation 14 into an electrical signal. Photo detector 20 can be a high efficiency solid-state detector device formed from silicon, InGaAs or a specially doped AlGaAs material having a narrow bandpass detection characteristic centered near or around 900 nm. Detector 20 is described in more detail with reference to FIGS. 13 and 14.

Radiometric system 10 further includes an amplifier 24 that receives the small electrical signal from photo detector 20 and amplifies the signal to a level suitable for further processing. Amplifier 24 of this invention allows measuring electrical signals as small as 10–16 amps.

Radiometric system 10 further includes an analog-to-digital converter ("ADC") 26 for converting the amplified electrical signal into a digital signal and a signal processor 28 for processing the digital signal into a temperature reading. The processing includes software algorithms employing the Planck equation.

Radiometric system 10 generates a high-speed digital output signal 30, which can be viewed as temperature measurements on a personal or host computer running conventional user software or, preferably, a Windows®-based user software product named TemperaSure™, which is available from Engelhard Corporation, located in Fremont, Calif.

Radiometric system 10 further includes a generally tubular housing 32 that encloses at least photo detector 20, amplifier 24, ADC 26, and signal processor 28. Housing 32 is preferably at least about 2.54 cm (1 inch) in diameter and at least about 10.16 cm (4 inches) long. Of course, the shape and dimensions of housing 32 may vary to suit different applications.

Figure 2:
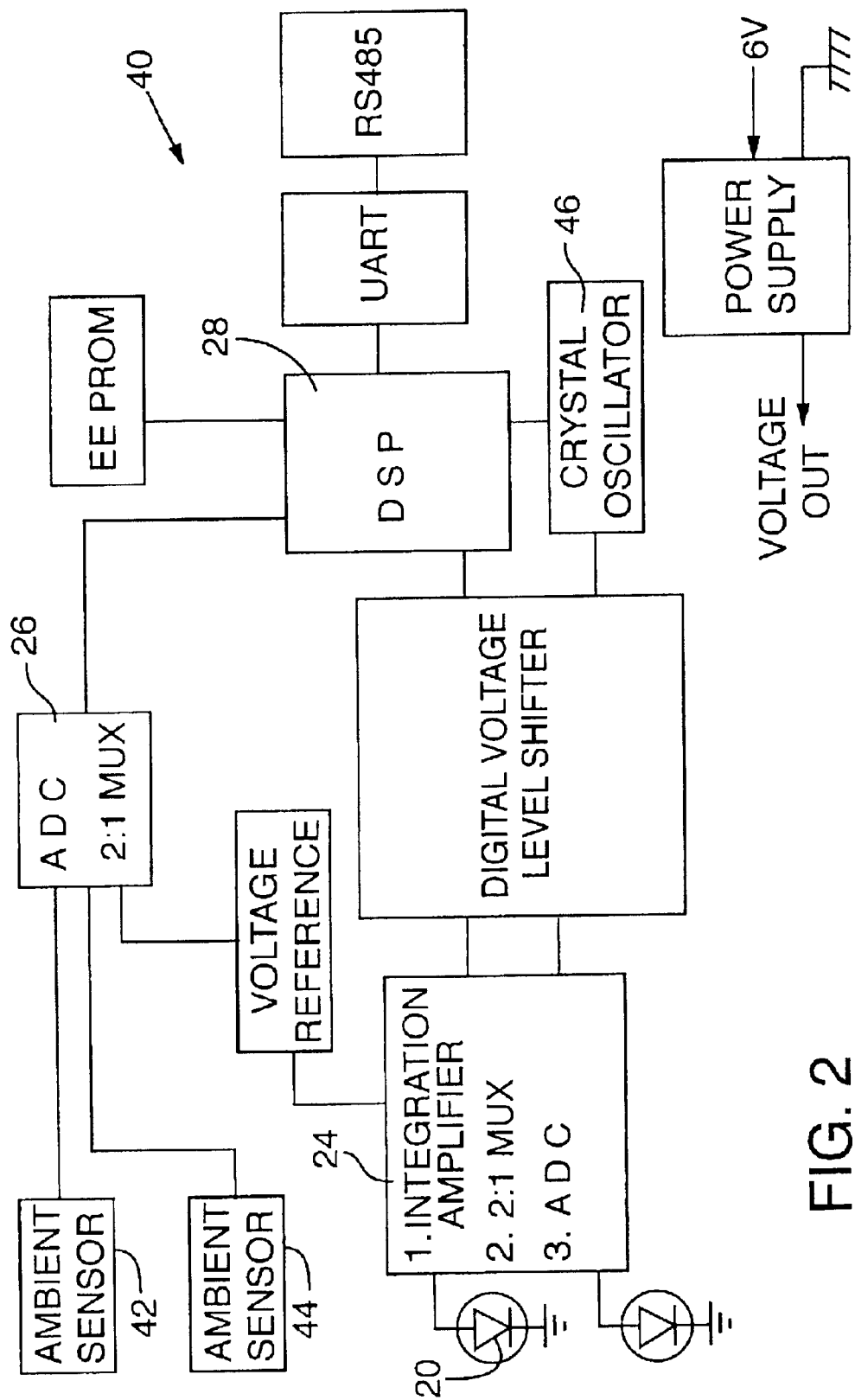
FIG. 2 is a simplified electrical block diagram of the electronic circuitry portion of the pyrometer system of this invention.

FIG. 2 shows a block diagram of electronic circuitry 40 portions of radiometric system 10, which circuitry is preferably included on a printed circuit board (not shown) that fits within housing 32. Electronic circuitry 40 utilizes significantly smaller components and arrays them in a highly compact format such that the overall instrument size is reduced dramatically from prior pyrometers. This form factor enables direct coupling of photo detector 20 and electronic circuitry 40 to collection optics 12 and, therefore, eliminates the undesirable fiber cable often found in prior optical thermometers. Eliminating the fiber cable in semiconductor temperature measurement applications reduces optical losses and signal variations.

Electronic circuitry 40 preferably includes photo detector 20 and an array of IC chips for amplifying and integrating (or averaging) the electrical signal generated by photo detector 20. Electronic circuitry further includes two or more temperature sensors 42 and 44 to monitor ambient temperatures of components, such as photo detector 20, amplifier 24, wavelength selective filter 18, and a timing circuit 46.

Compensating target temperatures based on information gained from sensors 42 and 44 accounts for deviations in component performance having differing temperature-dependent physical behaviors. For example, amplifier 24 gain changes with temperature as do the characteristics of photo detectors, analog to digital converters, timing oscillator crystals, and reference voltage or current sources. It is also beneficial to use an internal temperature sensor to monitor and compensate for the temperature of objects within the pyrometer system that occupy any part of the field of view ("FOV") of the photo detector.

Electronic circuitry 40, in combination with the techniques described herein, increases the signal-to-noise ratio of radiometric system 10 and allows temperature measurements to be made down to about 10° C. by measuring object emissions at or near 1,650 nm, and down to about 170° C. by measuring object emissions at slightly shorter than 1,000 nm. These conditions provide signal levels that have heretofore been too weak to measure accurately.

By comparison, the temperature measuring limits of prior optical radiometers operating at wavelengths shorter than, 650 nanometers, with ±5 degrees of noise, and a 1 Hz sampling bandwidth, is approximately 50° C. with a cooled/un-cooled indium gallium arsenide detector ("InGaAs"); or about 300° C. with a cooled/un-cooled silicon detector at 900 nm.

It should be noted that while the minimum temperature measuring limit is reduced by only a factor of two for the InGaAs detector and by a factor of about 1.6 for the silicon detector, the signal reduction at the detector is approximately a factor of 50 for the InGaAs detector and a factor of 3,000 for the equivalent silicon detector. This invention has enabled these minimum temperature measurement reductions through reducing optical losses, reducing or eliminating factors that cause signal level variations, and electronic signal processing improvements.

Figure 3:
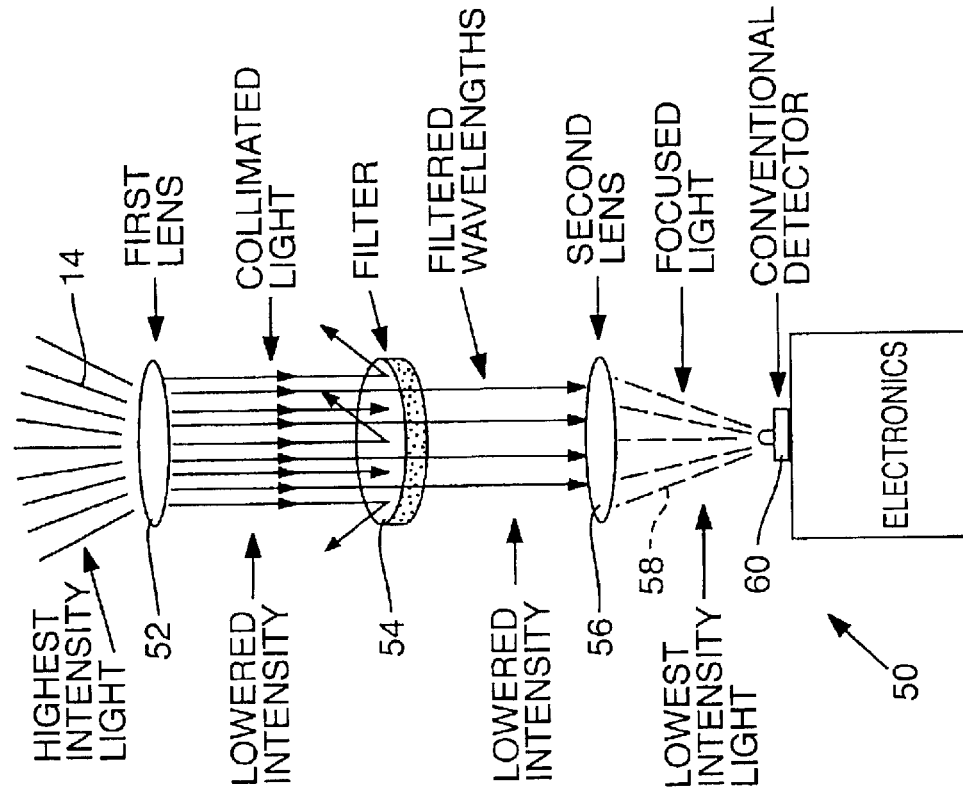
FIG. 3 is a simplified pictorial view of a prior art optical pyrometer employing a first lens for collimating radiation through a filter and a second lens for focusing the filtered radiation on a silicon detector.

Regarding improvements that reduce optical losses, FIG. 3 shows a prior art optical pyrometer 50 employing a first lens 52 for collimating radiation 14 through a wavelength selective filter 54 and a second lens 56 for focusing filtered radiation 58 on a conventional silicon detector 60. Wavelength selective filter 54 transmits a desired radiation wavelength and blocks unwanted wavelengths. For example, long wavelength blocking filters block light at long wavelengths while transmitting short wavelengths of light. Unfortunately, filters do not transmit the desired radiation wavelengths with 100 percent efficiency, which causes optical losses that adversely affect the measurement system sensitivity. Moreover, filters work best with collimated light, which usually requires multiple lenses to collimate the light through the filter and then focus it on the detector. The multiple lenses further reduce the amount of light that reaches the detector.

Figure 4:
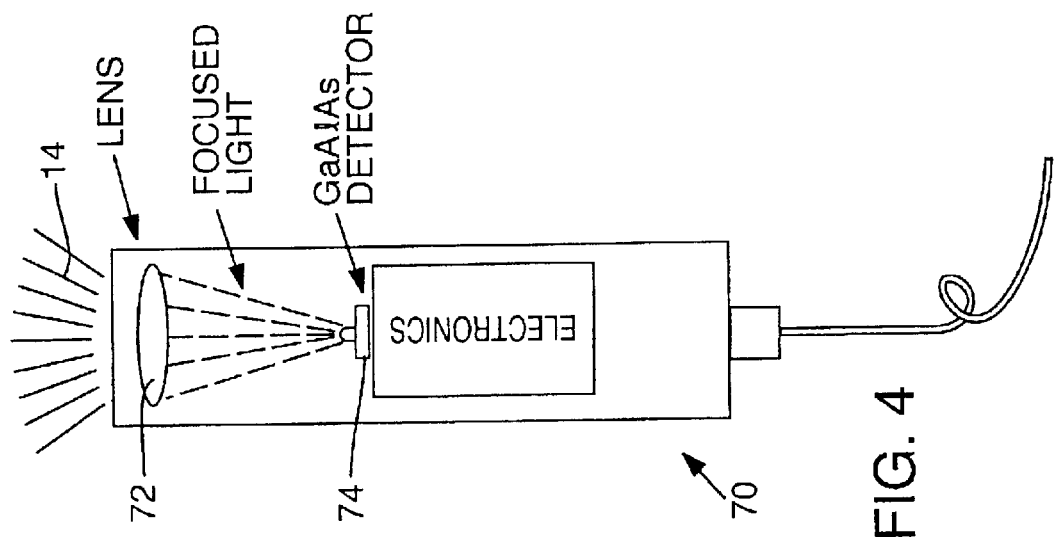
FIG. 4 is a simplified pictorial view of an optical pyrometer of this invention employing a single lens for focusing radiation on a wavelength selective AlGaAs detector.

In contrast, FIG. 4 shows an optical pyrometer 70 of this invention that employs a single lens 72 for focusing radiation 14 on a wavelength selective AlGaAs detector 74 of this invention. The wavelength selective filtering achieved by AlGaAs detector 74 has a rapidly diminishing response as wavelength increases, enabling a measurement system having increased sensitivity because the losses associated with filter 54 and second lens 56 are eliminated. Also the angled light does not effect the wavelength sensitivity of the AlGaAs detector.

Miniaturization of the detector/electronics system and direct coupling to the light capturing source further increase the measurement sensitivity of the pyrometers of this invention.

FIG. 5 shows a typical prior art pyrometer system 80 that employs a lens assembly 82 or a quartz or sapphire light guide rod 84 for collecting radiation 14 and propagating it onto an optical fiber or fiber bundle 86 for conduction to a detector 88. Light guide rod 84 or lens assembly 82 interfaces with the high temperature environment of the object. Optical fiber 86 isolates detector 88 and associated electronics 90 from electrical noise and heat and provides mechanical flexibility for placing detector(s) 88 in a convenient location. While this arrangement provides mechanical convenience, the following factors associated with using optical fibers 86 in semiconductor applications reduce their ability to accurately transmit radiation 14 to detector(s) 88:

If a single flexible fiber is employed to propagate radiation 14 from light guide rod (lightpipe) 84 to detector 88, then there will be large (~80%) optical losses due to the difference in index of refraction and the fact that the flexible fiber is usually smaller in diameter than the lightpipe. If, instead, a fiber bundle is employed to propagate the radiation from the light guide rod (lightpipe) to the detector, significant loss of optical signal strength will still result due to the mismatched index of refraction and the fill factor of the bundle (the spaces between fibers) being less than 100 percent.

Because of the limited availability of glass types from which to make optical fiber 86, it is nearly impossible to achieve a numerical aperture that is equivalent to the index of refraction of light guide rod 84.

Unless optical fiber 86 includes an antireflection coating, reflection losses will exist at the glass-to-air interfaces at the ends of optical fiber 86. The reflection losses are exacerbated if the index of refraction is raised in an attempt to capture all of the light from light guide rod 84.

Because optical fiber 86 can only contain radiation that is traveling over a limited range of angles, radiation 14 that is captured by lens assembly 82 or light guide rod 84 and propagated into optical fiber 86 will have a variable loss if optical fiber 86 is flexed.

As optical fiber 86 is heated or cooled, its transmission characteristics change causing transmitted signal variations.

When employing an optical fiber cable, errors are easily introduced at both ends of the cable: first, through misalignment of the cable ends when they are connected to the light guide rod 84 and photo detector 88, and secondly due to imperfect cleaning of the two surfaces. Moreover, when optical fiber 86 is attached and removed from the radiation collection system or detector 88, alignment changes can occur causing variations in the transmitted light.

By way of comparison, FIG. 6 shows that in this invention, the losses and signal variations associated with optical fibers are eliminated by eliminating optical fiber(s) 86 and directly coupling detector 20 to light guide rod 12 and/or detector 74 to lens 72 of respective pyrometers 10 (FIG. 1) and 70 (FIG. 4). To accomplish this in a mechanically effective way, the detector and supporting electronics are miniaturized as shown in FIG. 1 to fit into space-constrained locations.

As the device geometry of ICs becomes ever smaller, the measurement of lower temperatures becomes more critical for these processes. As temperatures decrease, the amount of radiation emitted by the wafer also decreases. Therefore, the radiation transmission efficiency of light guide rods coupled to detectors become ever more critical to accurate temperature measurements.

Moreover, as the price of IC's decreases, extreme cost-reduction pressure has been placed on semiconductor equipment manufacturers. Given the high cost of sapphire, the current state-of-the-art material for fabricating light guide rods, alternative materials have long been sought after for making light guide rods.

Accordingly, this invention includes an improved light guide rod material for reducing the optical losses encountered when employing optical pyrometry in, for example, semiconductor processing applications. This improved material is formed of aluminum oxide single crystal, the preferred type being YAG, which provides increased light transmission characteristics, resulting in improved low temperature measurement capabilities. A suitable alternative light guide rod material is yttrium aluminum perovskite ("YAP"). Recent processing improvements have allowed manufacturing YAG and YAP in rod lengths and form factors suitable for use in optical pyrometry applications.

YAG retains many of the benefits of sapphire, in that it is very similar in hardness (MOHS hardness of 8.2 vs. 9 for sapphire), melting point (1,965° C. vs. 2,050° C. for sapphire), and ability to withstand thermal shock. These unexpected benefits make YAG ideally suited for fabricating light guide rods 12 and 84 used in temperature sensing for semiconductor applications.

While YAG has been used for other optical applications such as in lasers, hitherto it could not be grown long enough and was usually doped, so it has never been considered as a potential light guide rod material. However, the increased demand for YAG for other applications resulted in major manufacturing advances, with producers now able to grow it in lengths up to one meter. This recent development and additional new research in un-doped YAG has led to the unexpected discovery of many properties that make YAG ideally suited for use in semiconductor applications. For example, when compared to sapphire, the YAG material:

reduces optical losses because of its higher index of refraction and better crystal structure;

reduces or eliminates factors which cause variations in the signal level due to lack of uniformity from light guide rod to light guide rod;

is less affected by surface contamination;

provides tighter machining tolerances;

reduces the light guide rod's thermal conductivity; and as opposed to sapphire, YAG is easier to machine into round rods because of its crystal structure.

Regarding reduced optical losses, YAG has a higher refractive Index, resulting in better radiation transmission. When fabricating light guide rods, a ferrule is attached to the light guide rod as a means of securing the rod to the pyrometer. An O-ring is also typically attached to the rod to provide a seal between the rod and the wafer-processing chamber into which the rod is inserted. However, when these parts contact the rod, radiation can be scattered at the contact points. Care must be taken, therefore, in selecting materials with a high refractive index to prevent radiation from scattering at the contact points. Accordingly, only sapphire and quartz rods and fibers have been used in prior semiconductor applications. While these materials provide a high refractive index, a consistent problem (particularly with quartz) has been that radiation is still scattered at the ferrule and O-ring contact points, thus reducing the light guide rod's transmission capabilities.

An improvement therefore would be to employ a material having characteristics similar to sapphire or quartz but with a higher refractive index to reduce the amount of scattered radiation at the contact points. Because YAG has a higher refractive index (1.83 at 632.8 nm) than sapphire or quartz, it is less sensitive to radiation losses at the contact points and is, therefore, ideally suited as an improved light guide rod material.

When fabricating light guide rods, it is important to obtain highly polished rod sides to prevent radiation from scattering out of the guide rod sides. Because quartz is a soft material it is difficult to prevent scratches on the sides of quartz rods. On the other hand, because sapphire is such a hard material, it is difficult to polish out all the scratches produced on sapphire rods during their manufacture.

YAG is harder than quartz but not quite as hard as sapphire, making it ideally suited for fine side polishing, thereby preventing radiation from scattering from the sides of YAG rods.

When fabricating IC's (which now have device geometries as small as 0.11 microns), it is critical that the IC manufacturing equipment be uniform from tool to tool. Consequently, each component of a semiconductor-fabricating tool must maintain a very high level of uniformity, including a high level of uniformity among light guide rods. YAG provides several unexpected benefits for providing such uniformity, which could not be achieved with sapphire or quartz. These benefits include:

YAG has no birefringence, so it provides more uniform light collection;

YAG is an isotropic material, so it eliminates problems with growth misalignment and/or machining misalignment that are common to sapphire; and YAG can be more easily machined to a tolerance as low as ±0.0001 inches, whereas sapphire can only be machined easily to a tolerance of ±0.001 inches.

The accuracy of pyrometers can be improved by preventing unintended heat from reaching the detector. When using light guide rods for transmitting radiation from the wafer to the detector, the light guide rod can itself become hot and conduct heat from the process chamber in addition to radiation from the wafer, causing temperature measurement errors. Consequently, the light guide rod should have a low level of thermal conductivity.

Fortunately, YAG has a lower level of thermal conductivity than sapphire. An additional benefit is that lower temperature epoxies can be used for securing ferrules to the YAG rods, and O-rings having lower heat resistance can be used.

Another series of improvements for facilitating the measurement of low temperatures is the reduction or elimination of factors causing signal level variations. A number of such factors have been identified, and techniques to improve or eliminate them have been developed as described below.

When using a light guide rod as a radiation collection system, the rod-to-detector coupling efficiency may be reduced by foreign matter that accumulates on the optical faces of the rod and detector. In particular, foreign particles can be deposited on the surfaces when the rod and detector are disconnected. In addition, the mechanical movement associated with connecting and disconnecting the rod deposits debris on the interface surfaces. This debris may adversely affect the measurement system calibration.

FIG. 7 shows a mounting system for prior art light guide rod 84 and detector 88 in which an optical face 92 of light guide rod 84 and an optical face 94 of detector 88 are recessed within a threaded housing 96. This configuration makes cleaning of optical faces 92 and 94 difficult and ineffective.

In contrast, FIG. 8 shows a mounting system of this invention for light guide rod 12 and detector 20 in which optical faces 100 of light guide rod 12 and detector 20 are flush to the edges of their respective housings 102 and 104 and are, therefore, closely coupled. The flush mounting of this invention facilitates easy and effective cleaning of optical faces 100. The close coupling also improves rod-to-detector optical coupling and, thereby, reduces signal transmission variations.

Referring again to FIG. 1, when taking temperature measurements with radiometric system 10, it is important to block undesirable wavelengths of radiation 14 to reduce errors introduced by heat build-up in filter 18 and detector 20 and to prevent damage to photo detector 20 caused by the undesired wavelengths. Undesired wavelengths of radiation 14 are typically blocked by using filters. Two improved ways of blocking undesired wavelengths are:

When a blocking filter, such as filter 18, performs its function by absorbing radiation, the absorbed energy causes filter 18 to increase in temperature, which changes the blocking characteristics of filter 18, altering the response of the measurement system, and resulting in temperature measurement errors. These errors can be prevented by introducing an additional blocking system for impeding undesirable wavelengths of radiation 14.

A preferred way of accomplishing this additional blocking is to place reflective hot/cold mirror surface 22 coating on filter 18. Hot/cold mirror surface 22 preferably causes minimal change in the spectral characteristics of filter 18 in the desired wavelengths yet transmits wanted wavelengths of radiation 14 while reflecting undesired wavelengths as undesired radiation 120.

Reflecting the undesired radiation 120 back through collection optics 12 (light guide rod or lens) to the location being measured on object 16 is advantageous for the following reasons: the temperature of object 16 is not significantly altered because much of radiation 14 is returned to object 16; and filter 18, photo detector 20, and the associated electronics are more stable because they are not unduly heated by radiation 14.

Figure 9:
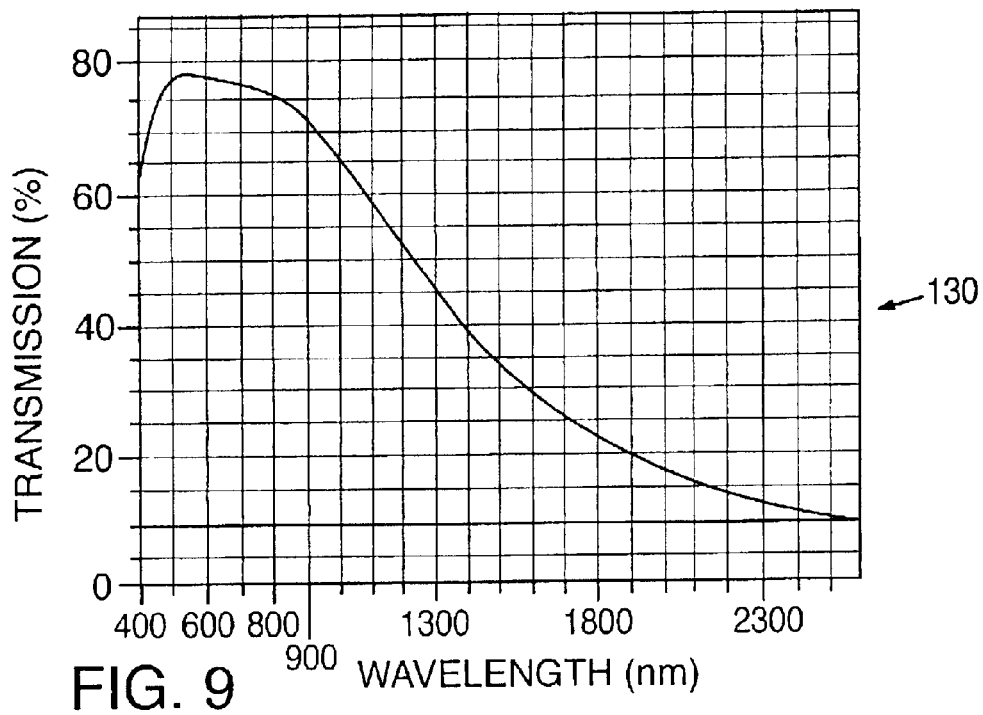
FIG. 9 is a graphical representation of a radiation transmission response as a function of wavelength for a reflective filter of this invention.

FIG. 9 shows a preferred response curve 130 for hot/cold mirror surface 22 of this invention. Hot/cold mirror surface 22 passes at least 70 percent of radiation 14 at about 900 nm and reflects substantial amounts of undesired radiation 120 at wavelengths above about 1,200 nm. Skilled workers will understand that hot/cold mirror surface 22 can be formed from a variety of suitable metallic and dielectric materials.

The response of a detector to radiation 14 and the electrical noise level it generates is a function of its operating temperature. Radiation wavelengths incident on the detector may not produce an electrical signal, but they may alter any existing signal by changing the detector temperature. In particular, short wavelength radiation may permanently alter the response characteristics of the detector. This radiation damage is prevented in part by the above-described hot/cold mirror surface 22 and also by filter 18, which further blocks unwanted radiation wavelengths from the detector. An advantage of the hot/cold mirror is that it prevents UV damage and IR heating, which causes a shift in the wavelength response of the photo detector and also causes electrical noise.

Figure 10:
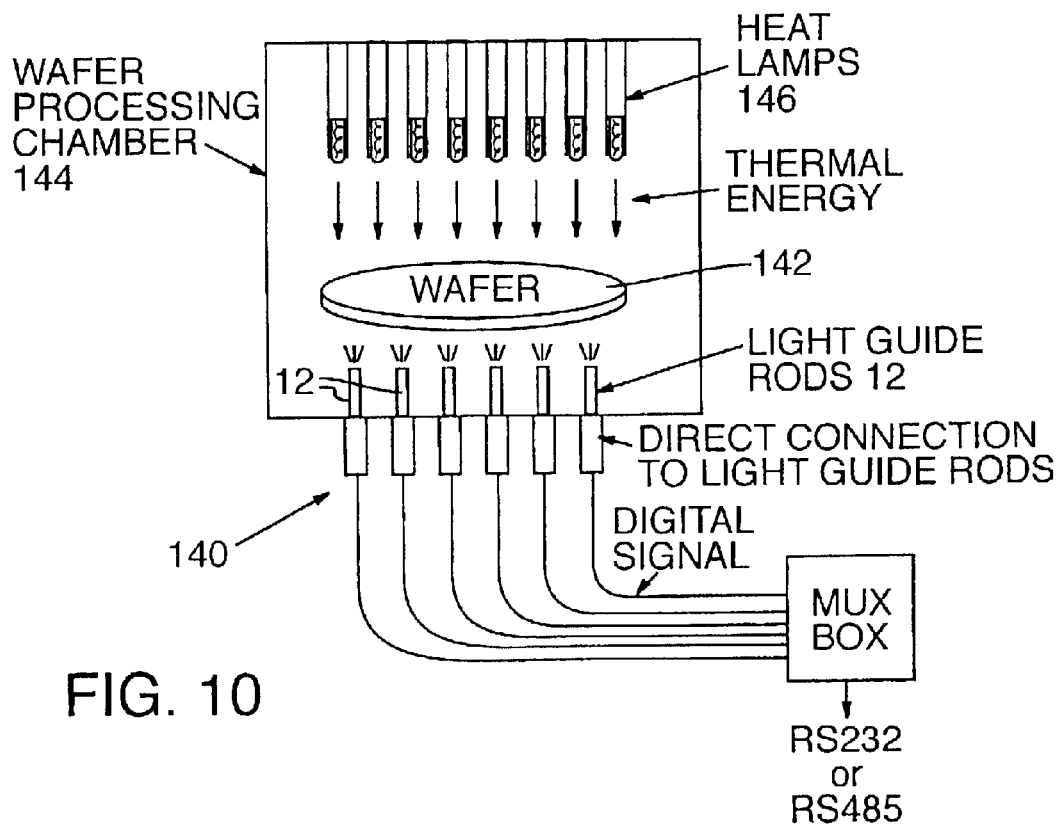
FIG. 10 is a simplified schematic pictorial view of a pyrometer system of this invention employed in a semiconductor process temperature measurement application.

FIG. 10 shows a pyrometer system 140 of this invention employed in a semiconductor processing application. A major application of pyrometer system 140 is measuring the temperature a silicon wafer 142 as it is heated in a processing chamber 144 by high-power lamps 146 or plasma (not shown). Lamps 146 are typically mounted on the opposite side of silicon wafer 142 from light collection optics 12.

Figure 11:
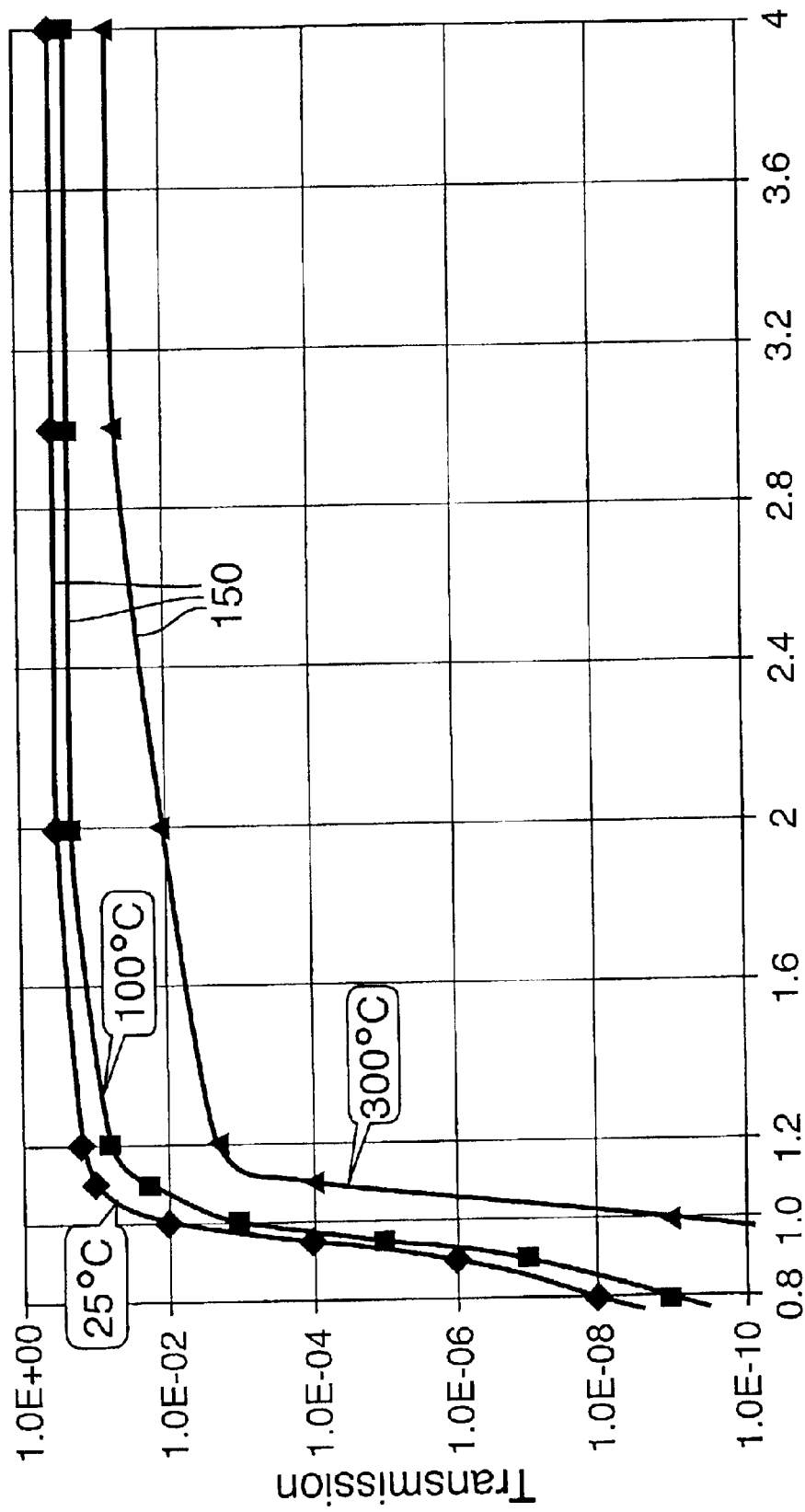
FIG. 11 are graphs representing the transmission of radiation through a silicon wafer as a function of wavelength and temperature.

FIG. 11, shows graphs 150 representing the transmission of radiation through a silicon wafer as a function of wavelength and temperature. Graph 150 shows that silicon wafer 142 is transparent to radiation beyond a wavelength of about 1,000 nm. Therefore, it is important to block radiation beyond 1,000 nm to prevent detector and filter heating that would cause temperature measurement errors. Several wavelength blocking techniques are aspects of this invention.

A common technique for achieving wavelength blocking is employing a short wavelength pass filter, which is fabricated by vacuum evaporation of optical materials having varying indices of refraction. By stacking a series of such materials, typically alternating high and low indices or refraction, a coating is produced that reflects or absorbs radiation over a limited range of wavelengths. To achieve blocking over a broad range of wavelengths, it is necessary to place successive stacks on top of each other such that each stack blocks a different wavelength range.

Figure 12A:
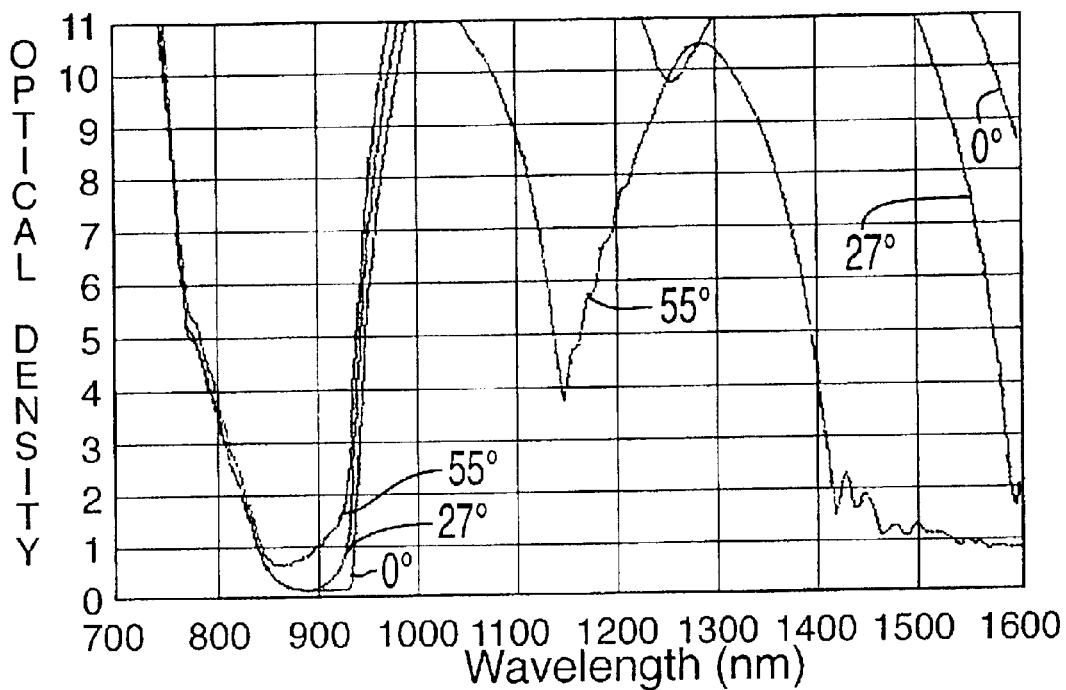
FIGS. 12A and 12B is graphs representing respectively the optical density and transmittance as a function of wavelength and radiation incidence angles of a short wavelength pass filter of this invention.
Figure 12B:
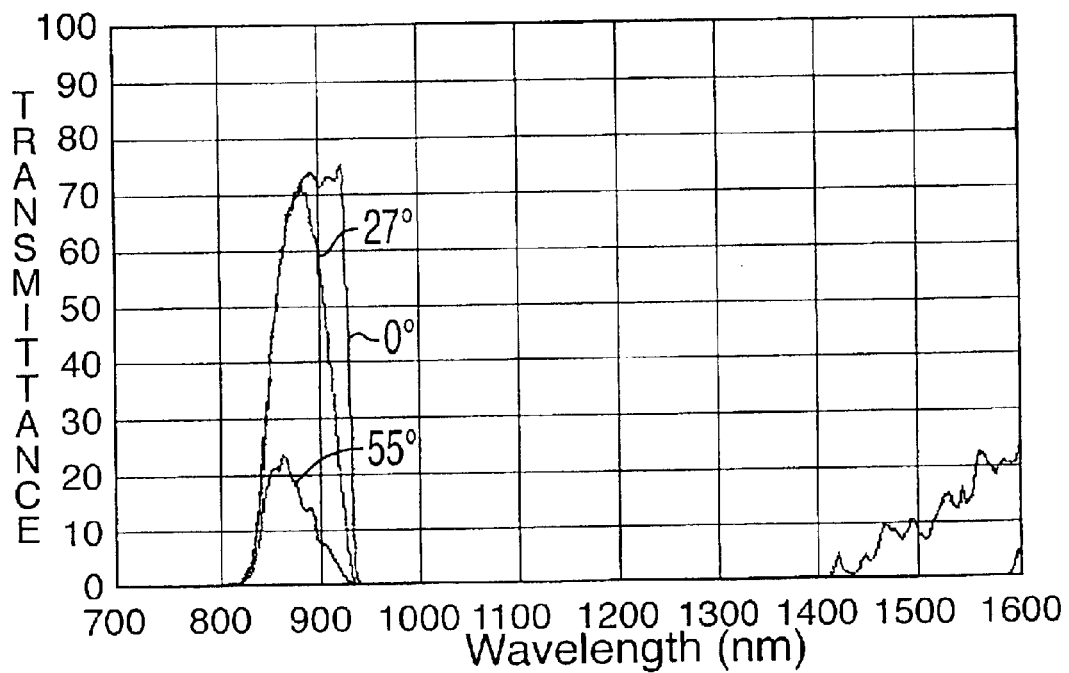

FIGS. 12A and 12B represent the respective optical density and transmittance versus wavelength and radiation incidence angle of a short wavelength pass filter that us suitable for use in this invention. Skilled workers will understand how to make such a filter. As shown in the graphs, this technique is most effective if the radiation is incident to the filter over a range of angles less than about 27 degrees. However, if the radiation is incident over a wide range of angles, e.g., up to about 55 degrees, the wavelength blocking characteristics are altered.

A suitable short wavelength pass filter, therefore, includes a blocking coating that includes as a design parameter the numerical aperture of the light guide rod or optical fiber that propagates the light from the sample to the detector.

Another embodiment of this invention employs gallium aluminum arsenide ("AlGaAs") and other wavelength-selective detector materials in place of band pass filters.

Figure 13:
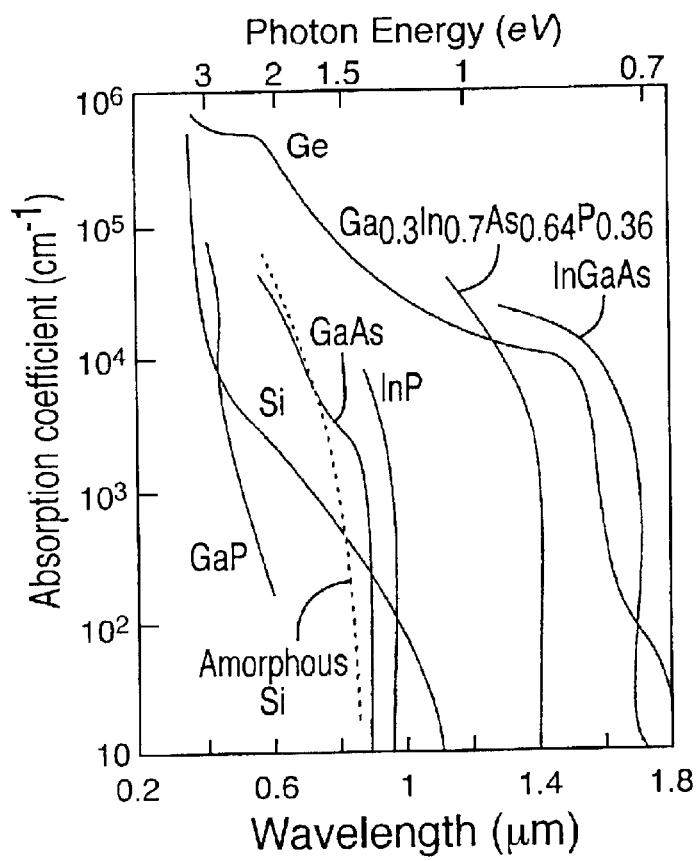
FIG. 13 is a graph representing the absorption coefficient of various detector materials as a function of wavelength.
Figure 14:
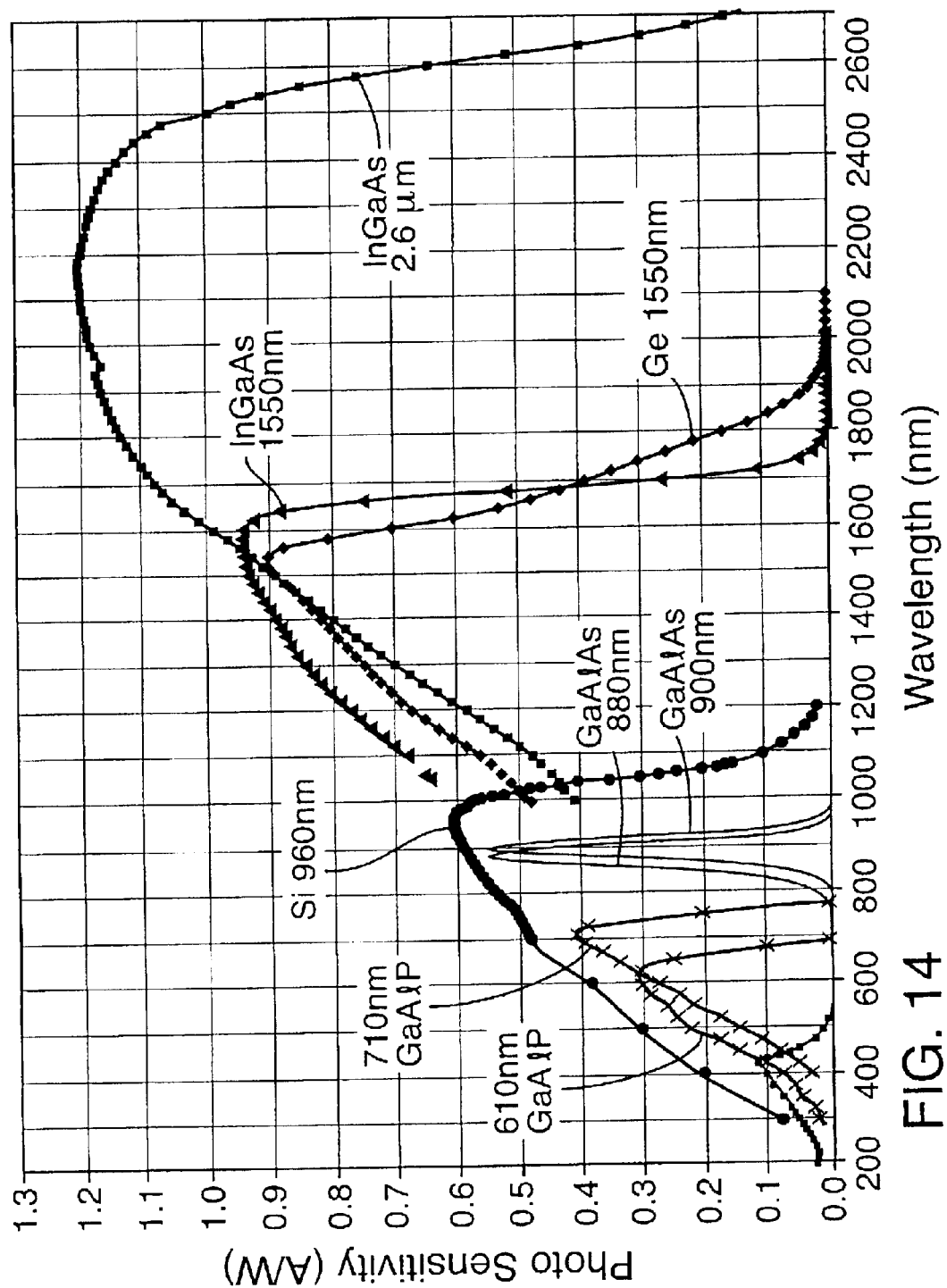
FIG. 14 is a graph representing the photo sensitivity of various detector materials as a function of wavelength.

FIGS. 13 and 14 represent the respective absorption coefficient and photo sensitivity of various detector materials as a function of wavelength. Conventional pyrometer detectors utilize either InGaAs or silicon detectors. InGaAs detectors are sensitive to radiation wavelengths as long as 2,700 nm, which makes blocking very difficult. Silicon detectors are nominally insensitive to wavelengths longer than 1,300 nm, however the photo sensitivity of silicon diminishes with longer wavelengths.

An aspect of this invention, therefore, is to utilize a detector material having a photo sensitivity that diminishes rapidly at wavelengths at which silicon wafers begin to transmit radiation. A preferred detector material is AlGaAs, which has a photo sensitivity peak at 900 nm and diminishes by about three orders of magnitude at 1,000 nm. Alternatively, detectors materials such as GaP, GaAsP, GaAs, and InP are suitable for use as wavelength-selective detectors at wavelengths less than 1,000 nm.

The photo detector materials for wafer temperature measurements are chosen for photo sensitivity around the optimum wavelengths for measuring silicon, GaAs, and InP wafers. In particular, the material is chosen for sensitivity at wavelengths shorter than the 1,000 nm (bandgap for silicon wafers), yet as long as possible to provide a maximum amount of Planck Blackbody Emission without significant sensitivity to radiation transmitted through the wafer.

The photo detector suitable for use with this invention is made from AlGaAs, a tertiary compound, and is doped to optimize its photo sensitivity around 900 nm. This detector material is advantageous because it is insensitive to radiation wavelengths transmitted through a silicon wafer, and to much visible ambient light. It is also advantageous because it has a narrow wavelength detection sensitivity, minimizing the need for an additional wavelength selective filter. A suitable detector is manufactured by Opto Diode Corporation, located in Newbury Park, Calif.

Of course, in situations where sharper cutoff is desired, the detector can be combined with a filter to achieve a wavelength selectivity compounding affect. In these situations, it is also easier to design and manufacture band pass filters that are matched for use with the particular detector material.

The ability to eliminate the filter altogether (along with the ability to use a simple band-pass filter when one is required) further allows the detector to be spaced much closer (0.25 mm verses 2.54 mm) to the light pipe, enabling collecting about ten times more radiation. The close spacing also provides better low temperature measurement performance, e.g., the ability to measure 200° C. compared to 350° C. with a traditional band-pass filter and a silicon broad band detector.

Figure 15:
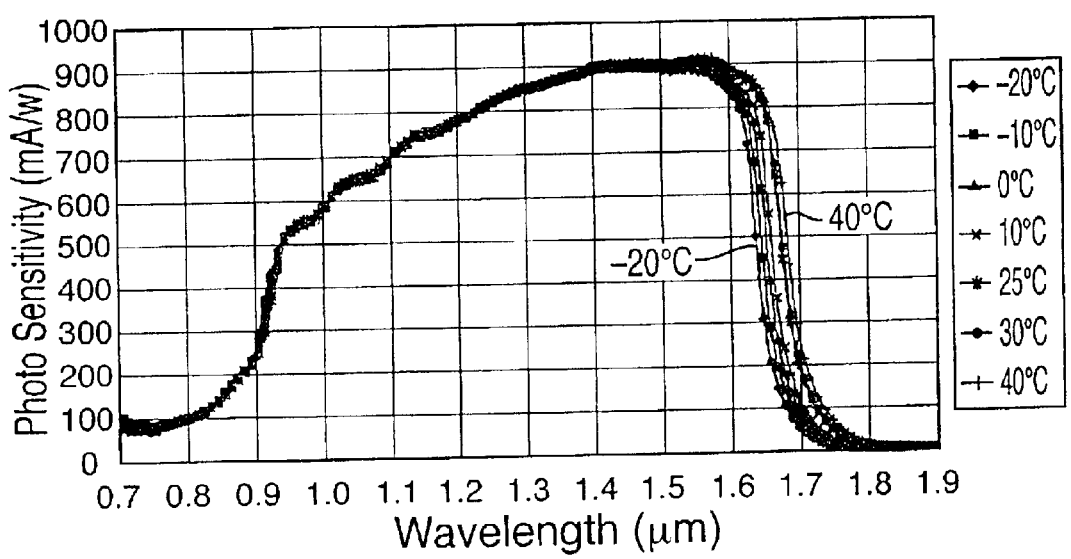
FIG. 15 is a graph representing photo sensitivity versus wavelength as a function of photo detector temperature.

As shown in FIG. 15, detector photo sensitivity changes with temperature, which causes output current variations that correspond to temperature measurement errors. Prior methods for dealing with this problem are to: 1) not correct for the error and simply specify a lower accuracy/repeatability specification; 2) use a band pass or cutoff filter to attenuate the detector wavelength selectivity skirts, thereby eliminating most of the spectral shifting variations; and 3) calibrate errors out by taking a set of measurements at various ambient and target temperatures and use the resulting data to extrapolate correction data.

Method 1 is clearly unacceptable for precision measurements.

Method 2 works well, although there are some remaining fluctuations caused by spectral shifts in the filter and detector. This method also significantly reduces the ability to measure lower temperatures because infrared wavelengths of interest are attenuated by the filter.

Method 3 also works well but is limited to the calibrated range of temperatures and is only relevant to systems of a similar configuration. The accuracy of this method is also limited by the conditions under which the data are taken and diminishes with higher target temperatures because of the difficulty of making accurate blackbody furnace measurements at these temperatures. In addition, this method is time consuming, limited in flexibility, and is not based on first principles of physics, making it prone to inaccuracies.

An improved method is to employ correction data generated from detector photo sensitivity curves as a function of wavelength, such as the curves shown in FIG. 15. A detector that is representative of the detectors used in a particular instrument model, is characterized with a monochromator at various ambient temperatures, such as 0, 10, 20, . . . 60 C., to generate a set of data. The data are then used to generate scale factor correction data for detector current vs. temperature using the Planck equation and integrating the area under the spectrum curve vs. target temperature.

The data entered into the software are ambient dependent detector spectrum curves, minimum theoretical target temperature, maximum theoretical target temperature, and one actual predetermined target temperature.

Figure 16:
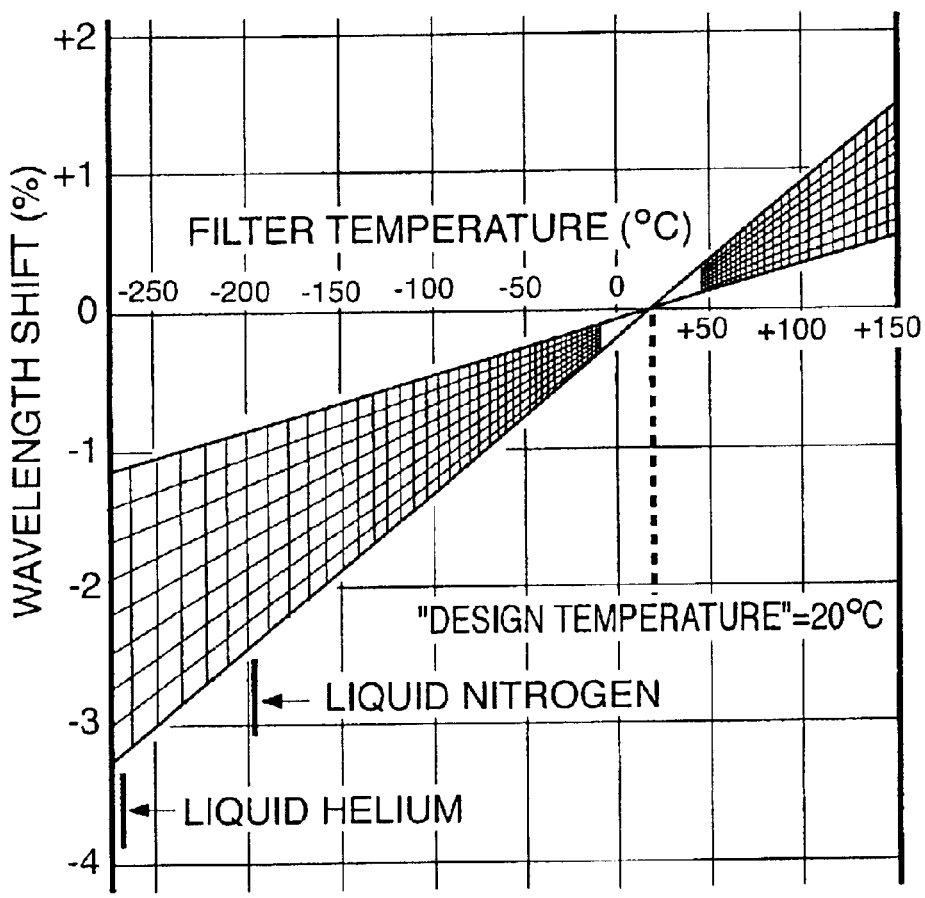
FIG. 16 is a set of graphs representing wavelength shift as a function of temperature for typical infrared interference filters.

This same correction method can be used for correcting for other optical components, such as optical filters that vary with ambient temperature. FIG. 16 shows a set of graphical data representing wavelength shift as a function of temperature for typical infrared interference filters. Suitable correction data can be extracted from such data.

Yet another series of improvements for facilitating the measurement of low temperatures are embodied in the software controlling the signal processing of this invention, and are set forth in the above-cited application Ser. No. 09/872,752.

Figure 17:
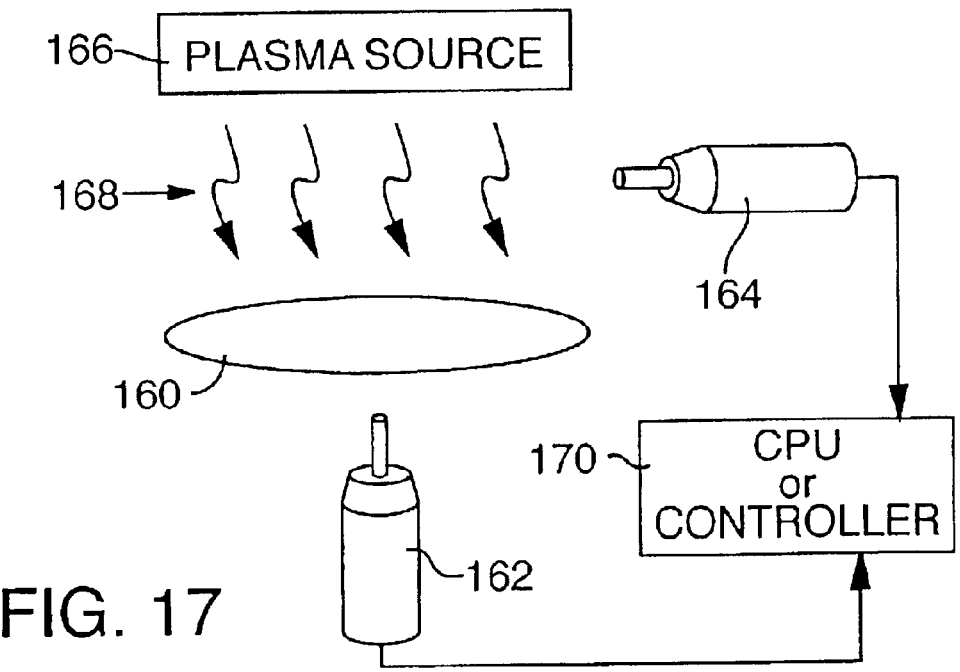
FIG. 17 is a simplified pictorial schematic view representing a semiconductor wafer temperature measurement being carried out in a plasma processing environment by employing an embodiment of a radiometric measurement system of this invention.

FIG. 17 shows a semiconductor wafer 160 undergoing an in-situ temperature measurement employing temperature measurement devices, such as pyrometers 162 and 164 of this invention. In-situ semiconductor wafer measurements are becoming common in IC fabrication facilities around the world. There are, however, numerous technical problems with measuring the temperatures of production wafers, such as wafer 160, when the Planck Equation is used to calculate its temperature from radiation emitted by a "hot" wafer.

There are three major problems encountered when measuring wafers at temperatures lower than 400° C.: First, very little signal is generated in the measuring device because the wafer emits only a small amount of light; second, the wafer tends to be more transparent at lower temperatures; and third, the background light signal is often larger than the light signal emitted by the wafer, and that background light enters the collection optics causing large measurement errors.

An embodiment of this invention employs pyrometers 162 and 162 in an improved measurement configuration and method for measuring the temperature of wafer 160 in plasma processes, such as for example, plasma etching, PVD, plasma strip, plasma cleaning, and plasma assisted chemical vapor deposition ("PECVD"). FIG. 17 shows a plasma source 166 generating a plasma 168 for etching wafer 160. This invention addresses the above-described three sources of measurement error as follows.

Pyrometers 162 and 164 receive radiation from, respectively, wafer 160 and background light from plasma 168 in a plasma etch, strip, or deposition process chamber. In particular, pyrometer 162 receives radiation from either the front or rear surface of wafer 160 (rear surface detection shown) during processing by plasma 168, and pyrometer 164 receives radiation from plasma 168. Preferably, both of pyrometers 162 and 164 are sensitive to about the same wavelength of received radiation. Two radiation wavelengths are preferred; 900 nm for about 200° C. to about 4,000° C. measurements, and 1,600 nm for about 25° C. to about 1,200° C. measurements.

A central processor unit or controller 170 receives signals derived from the photo diodes in pyrometers 162 and 164 and calculates a corrected wafer emission by employing the photo diode current relationship shown in Eq. 1:

$$I(\text{wafer uncorrected}) - K \cdot I(\text{plasma}) = I(\text{wafer emission}) \quad (1)$$

where, I is the photo diode current in amperes and K is a function that maps the amount of plasma radiation measured by photometer 164 (I(plasma)) to the amount of plasma radiation measured by pyrometer 162. K is determined empirically under known test circumstances, such as at known wafer temperatures, which gives a predicted I(wafer emission) based on the Planck equation and measured values for I(wafer uncorrected) and I(plasma), thereby allowing the Eq. 1 to be solved for K. Preferably, several tests are conducted under known conditions to determine a suitable value for K, which is then employed to determine I(wafer emission) under other conditions. The value of K is mostly a function of wafer transmission, and to a smaller degree, the viewing angles of the pyrometers. Often wafer transmission is unknown and changes with temperature and processing. Therefore, an additional pyrometer may be employed to empirically calculate the value of K.

The value of I(wafer emission) is then derived from Eq. 1 and employed in the Planck Equation to calculate the wafer temperature.

Figure 18:
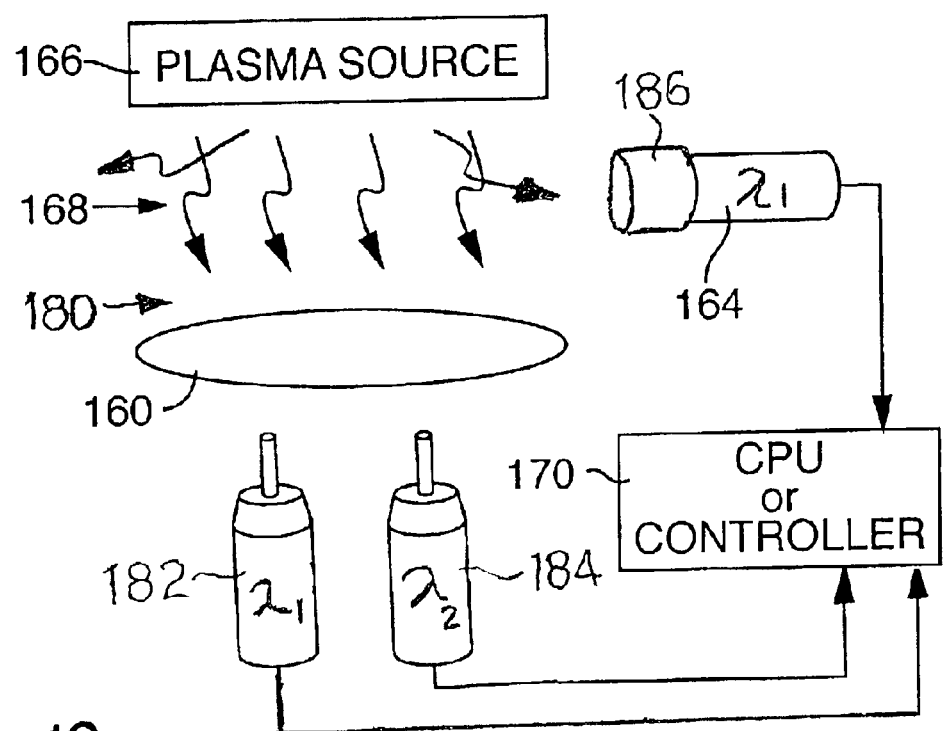
FIG. 18 is a simplified pictorial schematic view representing a semiconductor wafer temperature measurement being carried out in a plasma processing environment by employing an alternative embodiment of a radiometric measurement system of this invention.

FIG. 18 shows an alternate embodiment of this invention for use in situations in which access to an area 180 above wafer 160 is limited. In this alternative embodiment first and second pyrometers 182 and 184 are positioned beneath wafer 160. First pyrometer 182 is sensitive at a first wavelength suitable for detecting wafer radiation, and second pyrometer 184 is sensitive to a second wavelength suitable for detecting plasma radiation. In particular, the second wavelength is selected at a wavelength in which wafer 160 is substantially transparent to plasma radiation, whereas the first wavelength is selected at a wavelength in which wafer 160 is substantially opaque to plasma radiation. Therefore, first pyrometer 182 measures wafer 160 radiation and some transmission of plasma 168 radiation, and second pyrometer 184 measures mostly plasma 168 radiation transmitted through wafer 160 and a little radiation from wafer 160. The first wavelength may be, for example about 800 nm to about 1,300 nm, and the second wavelength may be, for example about 1,400 nm to about 2,600 nm. In this embodiment, pyrometer 164 preferably receives radiation at the first wavelength through a lens or light pipe assembly 186.

Skilled workers will recognize that portions of this invention may be implemented differently from the implementations described above for preferred embodiments. For example, alternative implementations may include employing a single pyrometer and rapidly switching the filter between the first and second wavelengths. Moreover, the description above applies primarily to temperature measurements of target media, but also applies to various forms of light measurements. Finally, skilled workers will also recognize that this invention is not limited to the advanced pyrometer described above, but can also be used to complement standard single-, dual-, or multi-wavelength pyrometry. It is also usable with temperature measurement devices other than pyrometers. Of course, these techniques can be used with both light pipes and/or light collection lens systems having one or more lenses.

It will be obvious that many changes may be made to the details of the above-described embodiments of this invention without departing from the underlying principles thereof. Accordingly, it will be appreciated that this invention is also applicable to temperature measurement applications other than those found in semiconductor processing.

The scope of this invention should, therefore, be determined only by the following claims.

We claim:

1. A method of measuring a temperature of a target medium undergoing processing in a gaseous medium, the target and gaseous mediums emitting electromagnetic radiations related to their temperatures, the method comprising:

sensing the electromagnetic radiations emitted by the target medium and the gaseous medium;

generating a first sensor signal value indicative of a sum of the electromagnetic radiations emitted by the target medium and the gaseous medium;

generating a second sensor signal value indicative of an amount of the electromagnetic radiation emitted by the gaseous medium;

empirically determining a value K relating a set of predetermined target medium temperatures to an associated set of first and second sensor signal values;

determining an amount of the electromagnetic radiation emitted by the target medium by subtracting K times the second sensor signal value from the first sensor signal value; and calculating the amount of the electromagnetic radiation emitted by the target medium to determine the temperature of the target medium.

2. The method of claim 1, in which the target medium includes a semiconductor wafer, and the gaseous medium includes a plasma.

3. The method of claim 1, in which the sensing is carried out by a pyrometer that is sensitive to first and second wavelengths of the electromagnetic radiations, and the first and second sensor signal values are derived substantially from electromagnetic radiations of the respective first and second wavelengths.

4. The method of claim 3, in which the target medium is substantially opaque at the first wavelength and substantially transparent at the second wavelength.

5. The method of claim 3, in which the pyrometer includes a switchable wavelength selective element that causes the pyrometer to alternately receive the first and second wavelengths of the electromagnetic radiation.

6. The method of claim 1, in which the sensing is carried out by a first pyrometer positioned to receive electromagnetic radiation emitted substantially by the target medium, and by a second pyrometer positioned to receive electromagnetic radiation emitted substantially by the gaseous medium.

7. The method of claim 6, in which the first pyrometer generates the first sensor signal values, and the second pyrometer generates the second sensor signal values.

8. The method of claim 6, in which at least one of the first and second pyrometers includes a probe element including a light guide formed from a material including single crystal aluminum oxide.

9. The method of claim 6, in which at least one of the first and second pyrometers includes collection optics comprising a lens or lens system.

10. The method claim 8, in which the light guide formed from single crystal aluminum oxide includes at least one of a yttrium aluminum garnet (YAG) and yttrium aluminum perovskite (YAP).

11. The method of claim 8, in which the light guide material includes at least one of quartz and sapphire.

12. The method of claim 1, in which the sensing is carried out by a solid-state detector material including gallium aluminum arsenide (AlGaAs).

13. The method of claim 12, in which the solid-state detector material includes a spectral response characteristic having a radiation response that peaks at about 900 nm.

14. The method of claim 1, in which the processing includes a plasma etch process.

15. The method of claim 1, in which the processing includes a physical vapor deposition process.

16. The method of claim 1, in which the processing includes a plasma strip process.

17. The method of claim 1, in which the processing includes a plasma cleaning process.

18. The method of claim 1, in which the processing includes a plasma assisted deposition process.

19. The method of claim 1, in which the calculating includes employing a Planck equation.

20. A method of measuring a temperature of a target medium undergoing processing in a gaseous medium, the target and gaseous mediums emitting electromagnetic radiations related to their temperatures, the method comprising:

sensing the electromagnetic radiations emitted by the target medium and the gaseous medium, the sensing being carried out by a pyrometer that is sensitive to first and second wavelengths of the electromagnetic radiations;

generating a first sensor signal value indicative of a sum of the electromagnetic radiations emitted by the target medium and the gaseous medium, the first sensor signal value being derived substantially from electromagnetic radiations of the first wavelength;

generating a second sensor signal value indicative of an amount of the electromagnetic radiations emitted by the gaseous medium, the second sensor signal value being derived substantially from electromagnetic radiations of the second wavelength;

empirically determining a value K relating a set of predetermined target medium temperatures to an associated set of first and second sensor signal values; determining an amount of the electromagnetic radiation emitted by the target medium by subtracting K times the second sensor signal value from the first sensor signal value; and calculating the amount of the electromagnetic radiation emitted by the target medium to determine the temperature of the target medium.

21. The method of claim 20, in which the target medium includes a semiconductor wafer, and the gaseous medium includes a plasma.

22. The method of claim 20, in which the target medium is substantially opaque at the first wavelength and substantially transparent at the second wavelength.

23. The method of claim 20, in which the pyrometer includes a switchable wavelength selective element that causes the pyrometer to alternately receive the first and second wavelengths of the electromagnetic radiations.

24. The method of claim 20, in which the calculating includes employing a Planck equation.

* * * * *